(12) United States Patent
Elgammal et al.

(10) Patent No.: US 12,417,845 B2
(45) Date of Patent: Sep. 16, 2025

(54) SYSTEM FOR AGGREGATING, ANALYZING, AND REPORTING MEDICAL INFORMATION

(71) Applicant: BioticsAI, Oakland, CA (US)

(72) Inventors: Hisham Elgammal, Alexandria (EG);
Robhy Bustami, Emeryville, CA (US);
Chaskin Saroff, San Jose, CA (US);
Salman Khan, Brentwood, CA (US)

(73) Assignee: BIOTICSAI, Oakland, CA (US)

(\*) Notice: Subject to any disclaimer, the term of this patent is extended or adjusted under 35 U.S.C. 154(b) by 448 days.

(21) Appl. No.: 17/657,970

(22) Filed: Apr. 5, 2022

(65) Prior Publication Data

US 2023/0317278 A1 Oct. 5, 2023

(51) Int. Cl.
*G16H 50/20* (2018.01)
*G16H 10/60* (2018.01)
*G16H 30/20* (2018.01)

(52) U.S. Cl.
CPC .............. *G16H 50/20* (2018.01); *G16H 10/60* (2018.01); *G16H 30/20* (2018.01)

(58) Field of Classification Search
CPC ......... G16H 50/20; G16H 10/60; G16H 30/20
See application file for complete search history.

(56) References Cited

U.S. PATENT DOCUMENTS

2020/0211692 A1\* 7/2020 Kalafut ................. G06N 20/00
2022/0071600 A1\* 3/2022 Canfield .............. A61B 8/5223

FOREIGN PATENT DOCUMENTS

GB 2614197 A \* 6/2023 .......... A61B 8/0866

OTHER PUBLICATIONS

Chen et al., Standard Plane Localization in Fetal Ultrasound via Domain Transferred Deep Neural Networks, 19(5) IEEE J of Biomedical and Health Informatics 1627-1636 (Sep. 2015) (Year: 2015).\*

Chaichanalap and Hanprasertpong, Success rate to complete optimal 20 + 2 ISUOG planes for foetal ultrasonographic structural screening during early second trimester pregnancy in Thailand, 13(36) The Ultrasound Journal 1-7 (Year: 2021).\*

Alexander Schmidt-Richberg et al, Abdomen Segmentation in 3D Fetal Ultrasound Using CNN-powered Deformable Models, Infant and Ophthalmic Medical Image Analysis 52-61 (Sep. 9, 2017) (Year: 2017).\*

(Continued)

*Primary Examiner* — Jordan L Jackson
(74) *Attorney, Agent, or Firm* — Vorys, Sater, Seymour and Pease LLP; Khaled Shami (57) ABSTRACT

In one embodiment, system for aggregating, analyzing, and reporting medical information includes a front end module for managing a user interface, a back end module for exchanging patient information with a clinic record system and obtaining one or more medical images therefrom, a machine learning/artificial intelligence (ML/AI) engine for analyzing said one or more medical images and generating analysis results, and a report generator for generating a report that includes the analysis results. The ML/AI engine can include an anatomical plane classifier such as a 20+2 classifier, and the anatomical structure classifier can apply sematic segmentation.

20 Claims, 7 Drawing Sheets

(56) References Cited

OTHER PUBLICATIONS

Liu et al., Efficient Patch-Wise Semantic Segmentation for Large-Scale Remote Sensing Images, 18 Sensors (Sep. 25, 2018) (Year: 2018).*

Jordina Torrents-Barrena et al., Segmentation and classification in MRI and US fetal imaging: Recent trends and future prospects, 51 Medical Image Analysis 61-88 (Year: 2019).*

* cited by examiner

SYSTEM FOR AGGREGATING, ANALYZING, AND REPORTING MEDICAL INFORMATION

CROSS-REFERENCE TO RELATED APPLICATIONS

Technical Field

The present disclosure relates generally to medical reporting systems.

Background

A number of diverse tools are increasingly called upon to track and manage medical information, such as that used by OB/GYN clinics for prenatal documentation, reporting and communication among medical care professionals and/or with patients. Conventionally, spreadsheets or stand-alone paper or electronic documents may be used by different employees responsible for different functions in an organization to store and maintain clinical reports, patient images and data, and other information. Such spreadsheets and stand-alone paper or electronic documents have a number of drawbacks. They can require significant overhead to maintain, have inaccurate data entries, or be unable to scale across different work units, organizations, or work flows.

Databases have been developed which can scale more easily and accommodate more data input from different users. Databases may even be part of a cloud-based service or network to allow remote users to access data more readily. In the medical field generally, and in prenatal ultrasound screening applications specifically, data storage systems include PACS (picture archiving and communication systems), and can also extend to some multipurpose HIS systems and to a limited extent EHR (electronic health record) systems. Such databases alone suffer from many of the drawbacks and limitations of spreadsheets when applied to the aggregation, analysis and reporting of medical information. They can require significant overhead to maintain, have inaccurate data entries, or be unable to scale across work units and organizations.

Cloud-based systems for generating reports have recently been introduced, but they too suffer from many drawbacks. For example, they fail to properly integrate the disparate information that may be relevant, such as patient initial information, biometric information, images and scans, diagnostic and analysis information obtained from the images and scans, and the relevant medical and administrative personnel involved. One reason for this failure is the different formats in which information is stored and then provided to the reports. Prior art reports also fail to establish the proper relationships of medical and other personnel who should be permitted access to the report or to whom the reports should be actively pushed, including for example specialists to whom the patient may be referred after identification of issues requiring their specialized expertise.

What is needed is a system for aggregating, analyzing, and reporting medical information that overcomes these and other limitations and drawbacks, by being able to integrate disparate forms of information retrieved seamlessly from patient data storage systems such as PACS using communication channels such as DICOM, and to organize and classify the information in reports in a clear format legible and useful to different users with different levels of medical training and background.

OVERVIEW

The present disclosure overcomes the above deficiencies and technical problems. In certain embodiments, the present disclosure provides new computer-implemented systems, methods and storage devices configured as a system for aggregating, analyzing, and reporting medical information.

In an embodiment, a system is configured to enable users to communicate over a data network with applications on remote computing devices accessed by users through user-interfaces.

In one embodiment, the system is implemented in a cloud computing system.

In further embodiments, computer-implemented methods for enabling a group of users to aggregate, analyze and report medical information through control inputs at user interfaces and non-transitory computer-readable storage devices.

Further embodiments, features, and advantages of the invention, as well as the structure and operation of the various embodiments of the invention are described in detail below with reference to accompanying drawings.

In certain embodiments, the system for aggregating, analyzing, and reporting medical information can be used for example by OB/GYN clinics for prenatal documentation, reporting and communication between medical care professionals and/or with patients or other laypersons. In certain embodiments, artificial intelligence (A.I.) is used to automate report generation for fetal ultrasound anatomical scans. Additionally, to ensure quality reporting, in certain embodiments, the AI flags ultrasound images that may have image quality issues (e.g: poor visibility due to acoustic shadowing). Other applications, such as detecting and flagging potential abnormalities, are also contemplated.

Certain applications of the system are medical practices and clinical departments, providing such utility as diagnostic interpretation of images, electronic documentation of examinations in the form of text and images, and generation of medical reports primarily for diagnostic ultrasound.

In certain embodiments, the system provides a user the ability to incorporate images, drawings, and charts into medical reports. It can accept, transfer, display, store, and process medical images and data, and enables the user to measure and annotate images. In certain embodiments, the displayed medical images can be used for diagnostic purposes.

In certain embodiments, users of the system include, but are not limited to,
OB/GYN Doctors
Midwives
Ultrasound Technicians/Sonographers
Radiologists
OB/GYN Nurses
OB/GYN Students/Residents

BRIEF DESCRIPTION OF THE DRAWINGS

The accompanying drawings, which are incorporated into and constitute a part of this specification, illustrate one or more examples of embodiments and, together with the description of example embodiments, serve to explain the principles and implementations of the embodiments.

In the drawings.

DESCRIPTION OF EXAMPLE EMBODIMENTS

Example embodiments are described herein in the context of a system for aggregating, analyzing, and reporting medical information. The following description is illustrative only and is not intended to be in any way limiting. Other embodiments will readily suggest themselves to those of ordinary skill in the art having the benefit of this disclosure. Reference will be made in detail to implementations of the example embodiments as illustrated in the accompanying drawings. The same reference indicators will be used to the extent possible throughout the drawings and the following description to refer to the same or like items.

In the description of example embodiments that follows, references to "one embodiment", "an embodiment", "an example embodiment", "certain embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. The term "exemplary" when used herein means "serving as an example, instance or illustration." Any embodiment described herein as "exemplary" is not necessarily to be construed as preferred or advantageous over other embodiments.

In the interest of clarity, not all of the routine features of the implementations described herein are shown and described. It will be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

In accordance with this disclosure, the components, process steps, and/or data structures described herein may be implemented using various types of operating systems, computing platforms, computer programs, and/or general purpose machines. Devices of a less general purpose nature, such as hardwired devices, field programmable gate arrays (FPGAs), application specific integrated circuits (ASICs), or the like, may also be used without departing from the scope and spirit of the inventive concepts disclosed herein. Where a method comprising a series of process steps is implemented by a computer or a machine and those process steps can be stored as a series of instructions readable by the machine, they may be stored on a tangible medium such as a computer memory device (e.g., ROM (Read Only Memory), PROM (Programmable Read Only Memory), EEPROM (Electrically Eraseable Programmable Read Only Memory), FLASH Memory, Jump Drive, and the like), magnetic storage medium (e.g., tape, magnetic disk drive, and the like), optical storage medium (e.g., CD-ROM, DVD-ROM, paper card, paper tape and the like) and other types of program memory.

Herein, reference to a computer-readable or machine-readable storage medium encompasses one or more non-transitory, tangible storage media possessing structure. As an example and not by way of limitation, a computer-readable storage medium may include a semiconductor-based circuit or device or other IC (such, as for example, a field-programmable gate array (FPGA) or an ASIC), a hard disk, an HDD, a hybrid hard drive (HHD), an optical disc, an optical disc drive (ODD), a magneto-optical disc, a magneto-optical drive, a floppy disk, a floppy disk drive (FDD), magnetic tape, a holographic storage medium, a solid-state drive (SSD), a RAM-drive, a SECURE DIGITAL card, a SECURE DIGITAL drive, or another suitable computer-readable storage medium or a combination of two or more of these, where appropriate. Herein, reference to a computer-readable storage medium excludes any medium that is not eligible for patent protection under 35 U.S.C. § 101. Herein, reference to a computer-readable storage medium excludes transitory forms of signal transmission (such as a propagating electrical or electromagnetic signal per se) to the extent that they are not eligible for patent protection under 35 U.S.C. § 101. A computer-readable non-transitory storage medium may be volatile, nonvolatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

Figure 1:
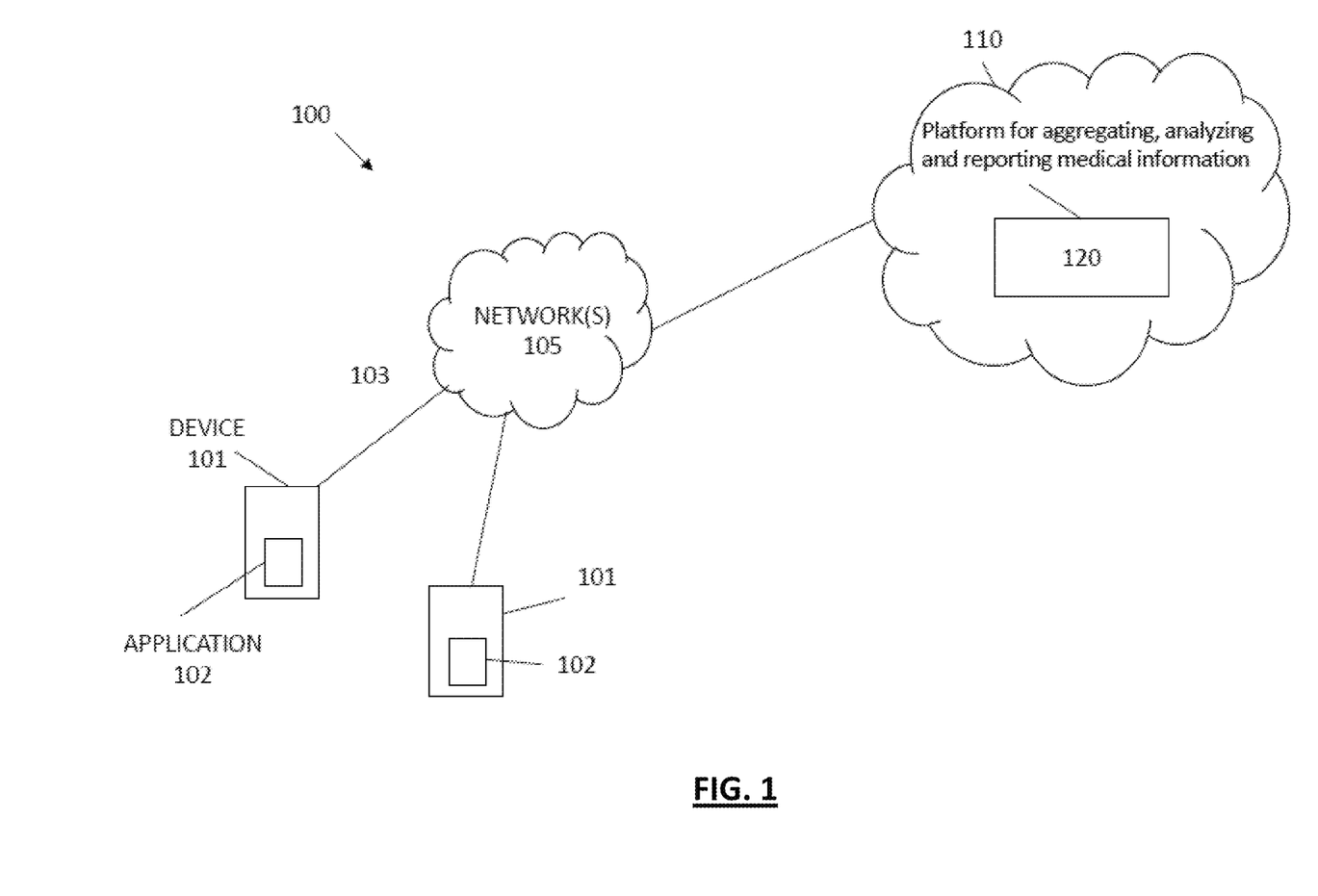
FIG. 1 is a diagram of a system 100 for aggregating, analyzing, and reporting medical information according to an embodiment of the present invention.

FIG. 1 is a diagram of a system 100 for aggregating, analyzing, and reporting medical information according to an embodiment of the present invention. System 100 includes one or more computing devices 101 coupled over communication links 103 and over one or more data networks 105 to a remote cloud computing system 110. Each computing device 101 may include an application 102. Remote cloud computing system 110 includes a platform 120 for aggregating, analyzing, and reporting medical information. Platform 120 may be implemented on one or more computing devices and communicatively coupled to applications 102 over data network(s) 105. Data network 105 may be any type of data network or combination of data networks covering a local area, medium area or large area (such as the Internet). Communication links 103 may be wired or wireless links.

In certain embodiments, the term application (such as application 102) refers to a desktop or laptop computer device application, mobile device application, web application, browser, or browser extension. For example, application 102 may be configured as an application installed on computing device 101 or may be a web application operated through a browser or browser extension on computing device 101 or a mobile phone application executing on an IOS or Android operating system. It can also refer to executable code run by medical devices such as an ultrasound machine that may be coupled to a hospital PACS system.

Figure 2:
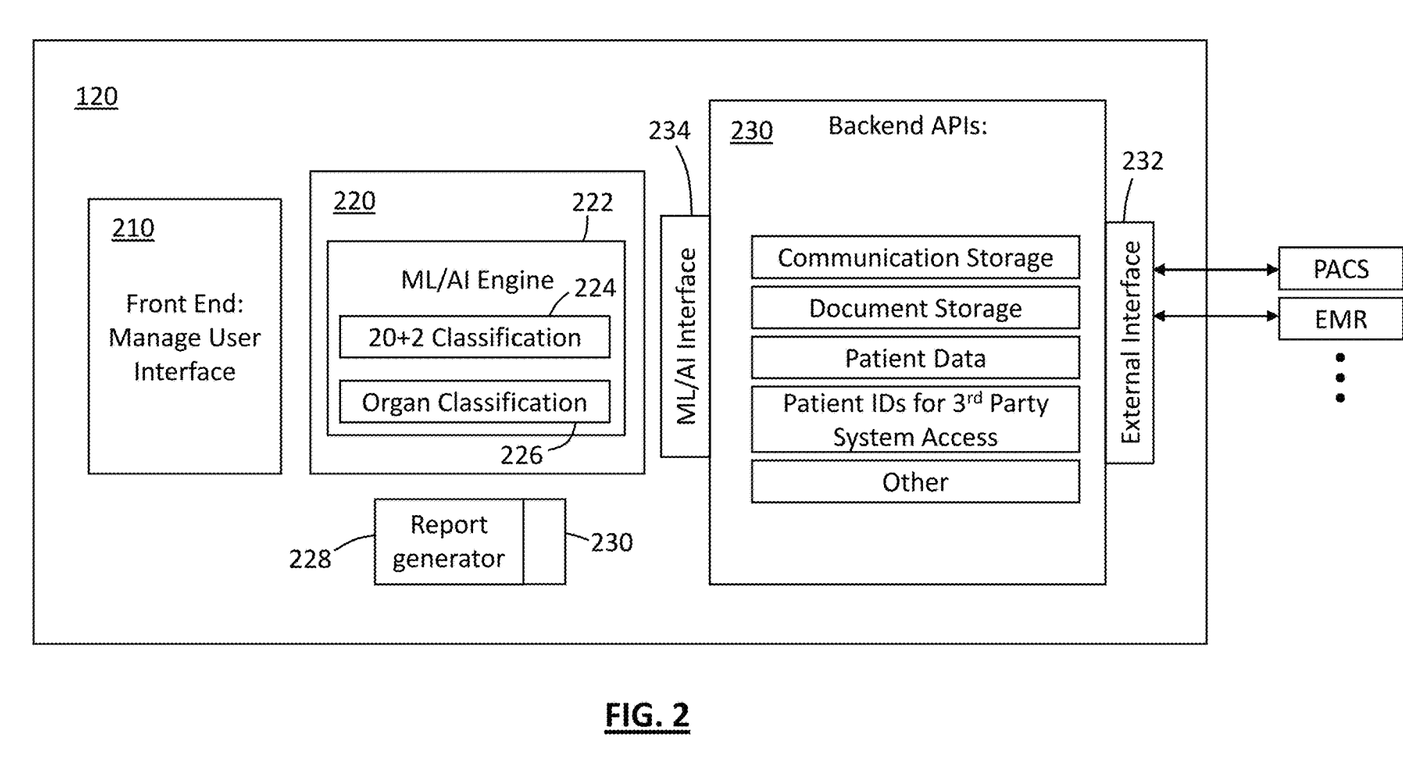
FIG. 2 is a diagram showing details of platform 120 for aggregating, analyzing, and reporting medical information according to certain embodiments.

FIG. 2 is a diagram showing details of platform 120 for aggregating, analyzing, and reporting medical information according to certain embodiments. Platform 120 includes three subsystems 210, 220, 230 coupled to one another. Front end subsystem 210 can be a module that is operable to manage a user interface (not show), whereby users such as those listed above can interact with the system, for example to view information, or to add or extract information therefrom. In certain embodiments, subsystem 210 manages user interface logic and for example includes code (not shown) to help render a list of images to the user in a user-friendly manner.

Platform 120 also includes backend subsystem 230. Backend subsystem 230 can be a module that includes API-based functionality that in certain embodiments can be activated from front end subsystem 210. In certain embodiments, features that APIs of subsystem 210 can be programmed to provide include storage of information such as communications between healthcare professionals, high level patient data, and patient IDs associated with the clinic's PACS (picture archiving and communication systems) and EMR (electronic medical records) systems. Such stored information can be included in the generated reports described below, in whole or in part. In certain embodiments, the backend subsystem 230 integrates with a clinic's records system(s) for exchange of information therewith by way of an external interface 232. This can be with the clinics' PACS and EMR system(s) or example, for performing data retrieval and processing from these systems, also optionally for inclusion in the reports in whole or in part. The PACS and EMR systems with which it integrates may be cloud-based or on-premises. In certain embodiments, the integration with a clinic's PACS system is over the DICOMWeb API. This can be done through a TLS (transport layer security) encrypted connection over a public network, within the clinic's private network (for an on-premises or clinic's cloud deployment environment), or over a VPN connection.

In certain embodiments, DICOM studies and DICOM structured reports are imported into the system 100 and DICOM studies and DICOM structured reports can be exported back into the clinic's PACS system.

In certain embodiments, backend subsystem 230 integrates with EMR systems over the HL7 FHIR API. This can be done through a TLS encrypted connection over a public network, within the clinic's private network (for an on-premises or clinic's cloud deployment environment), or over a VPN connection. Patient information can be imported into the platform and reports can be exported into the EHR system.

The subsystem 230 also integrates with ML (machine learning)/AI (artificial intelligence) subsystem 220, discussed below, for inference of ultrasound images and other operations. For example, backend subsystem 230 can be configured to make database queries to determine what information needs to be returned to the front-end subsystem 210 when the user clicks a particular button in a display or keyboard (not shown), or performs similar selection action.

As mentioned above, platform 120 also includes ML (machine learning)/AI (artificial intelligence) subsystem 220, coupled with backend subsystem 230 via ML/AI interface 234. ML/AI subsystem 220 interacts with the backend subsystem 230 and includes an API for receiving input data (DICOM studies consisting of ultrasound images and videos for example) and returning low-risk inference information (such as anatomical region classification) with a machine learning model rigorously trained and tested on fetal ultrasound data. In certain embodiments, detecting and flagging potential fetal abnormalities can also be performed in conjunction with ML/AI subsystem 220.

In certain embodiments, ML/AI subsystem 220 comprises an ML/AI engine 222 having classifier modules 224 and 226 that are responsible for accepting input data points (for example video or a picture) and returning two outputs:

1. The anatomical plane associated with each image (or frame in a video), as determined by the 20+2 classifier 224, and
2. The key anatomical regions and their location in the image (specified by annotating the pixels in the image that represent a key anatomical region), as determined by the anatomical structure classifier 226.

The "20+2" planes classification performed by classifier 224 conforms to the standard recommended by the International Society of Ultrasound in Obstetrics and Gynecology (ISUOG), an organization that delivers training and educational resources to OB/GYN practitioners in 140 countries. The "20+2" standard is included as part of the ISUOG's "Basic Training Programme" taught across worldwide ISUOG conferences and events. The following linked information below provides more detail into the standard itself and incorporated herein by reference:

The 20 Planes Approach to the Routine Mid Trimester Scan, ISUOG Basic Training, Trish Chudleigh, United Kingdom, 2018.

Lecture 15: The 20+2 planes approach to the routine mid-trimester scan, ISUOG Basic Training Programme, Trish Chudleigh, Singapore, October 2018.

Lecture 20: The 20 Planes Approach to the Routine Mid Trimester Scan, ISUOG Basic Training, Trish Chudleigh, Vienna, 2017

The "20+2" planes classification performed by classifier 224 conforms to the standard recommended by the International Society of Ultrasound in Obstetrics and Gynecology (ISUOG), an organization that delivers training and educational resources to OB/GYN practitioners in 140 countries. The "20+2" standard is included as part of the ISUOG's "Basic Training Programme" taught across worldwide ISUOG conferences and events. The following linked information below provides more detail into the standard itself and incorporated herein by reference:

The 20 Planes Approach to the Routine Mid Trimester Scan, ISUOG Basic Training, Trish Chudleigh, United Kingdom, 2018.

Lecture 15: The 20+2 planes approach to the routine mid-trimester scan, ISUOG Basic Training Programme, Trish Chudleigh, Singapore, October 2018.

Lecture 20: The 20 Planes Approach to the Routine Mid Trimester Scan, ISUOG Basic Training, Trish Chudleigh, Vienna, 2017.

Figure 2A:
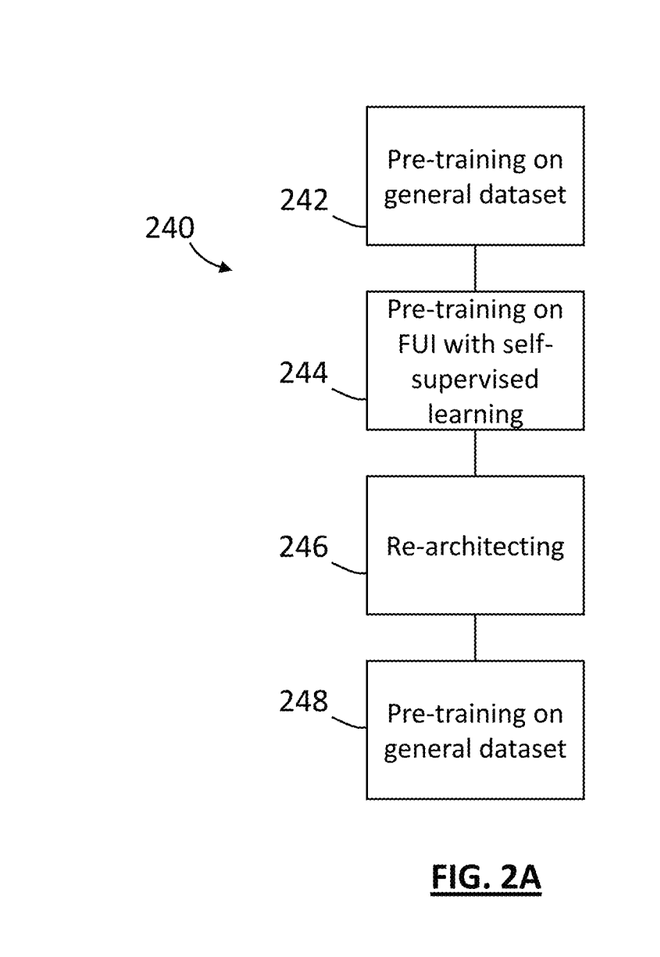
FIG. 2A shows a method for generating weights for matrices in accordance with certain embodiments.

An example method 240 for generating weights for matrices is illustrated in FIG. 2A, and includes, at 242, system pre-training on a large general public image dataset, additional pre-training on a general fetal ultrasound image dataset using self-supervised learning at 244, re-architecting at 246 final layers of a pre-trained convolutional neural network from steps 242 and 244 above to create multiple output heads to classify fetal planes, fetal abnormalities, fetal anatomical structures, and diagnostic utility (quality of the ultrasound image), and fine-tuning using an annotated dataset of second trimester fetal ultrasound images at 248.

Figure 2B:
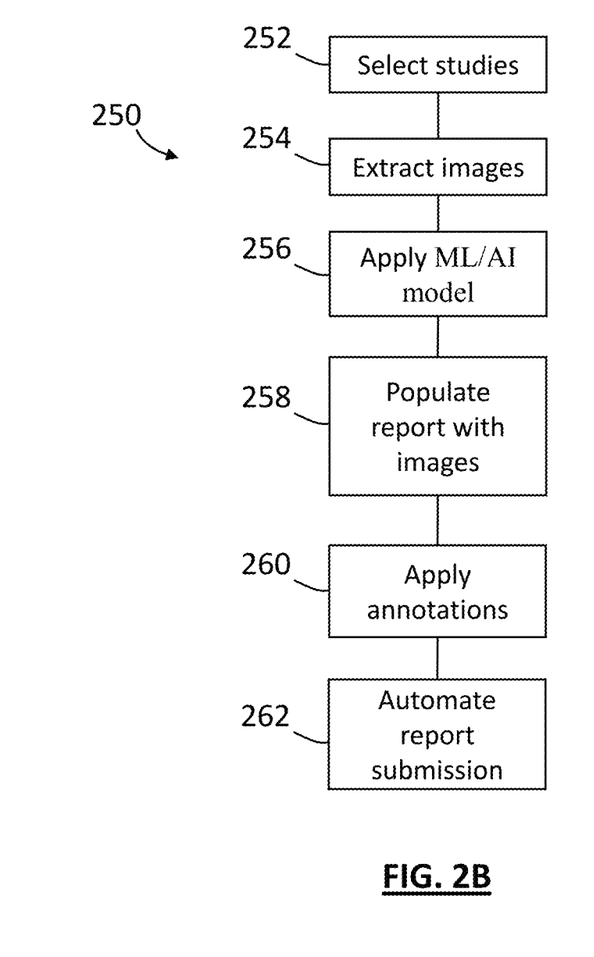
FIG. 2B shows a method a method performed by built software features to automate report generation in accordance with certain embodiments.

In certain embodiments, a proprietary dataset is created by annotating the data with:
1) 20 standard 2D fetal anatomical planes (ISUOG 20+2 Planes standard for ultrasound screenings)
2) Diagnostic clarity
3) Abnormalities
4) Specific pixel locations of anatomical structures In certain embodiments, software features built to automate report generation perform the method 250 shown in FIG. 2B, which includes, at 252, automatically selecting DICOM studies from a hospital's PACS system through automated polling of the DICOMWeb API; extracting, at 254, all images from the DICOM files; processing, at 256, the extracted images with ML/AI model described above; populating, at 258, the report with the images classified by the ML/AI model output, populating, at 260, the report with documented annotations specified by the ML/AI model output; and automating, at 262, report submission to required obstetric physicians and other personnel for review.

In certain embodiments, if the input is a video, ML/AI engine 222 analyzes the video and returns an output that includes timestamps that indicate the start and end of each anatomical plane. In certain embodiments, to ensure quality reporting, ML/AI engine 222 can flag ultrasound images that may have image quality issues, such as poor visibility due to acoustic shadowing. System 220 benefits from ML/AI engine 222 in this manner to improve the technology of assessing and reporting medical information by eliminating low quality images from analysis and thereby streamlining the reporting and analysis processes, reducing the time and computational effort required to generate reports. It also advances medical reporting technology by applying specific ML/AI rules in the classification of fetal images, eliminating subjectivity of human operators.

Figure 3:
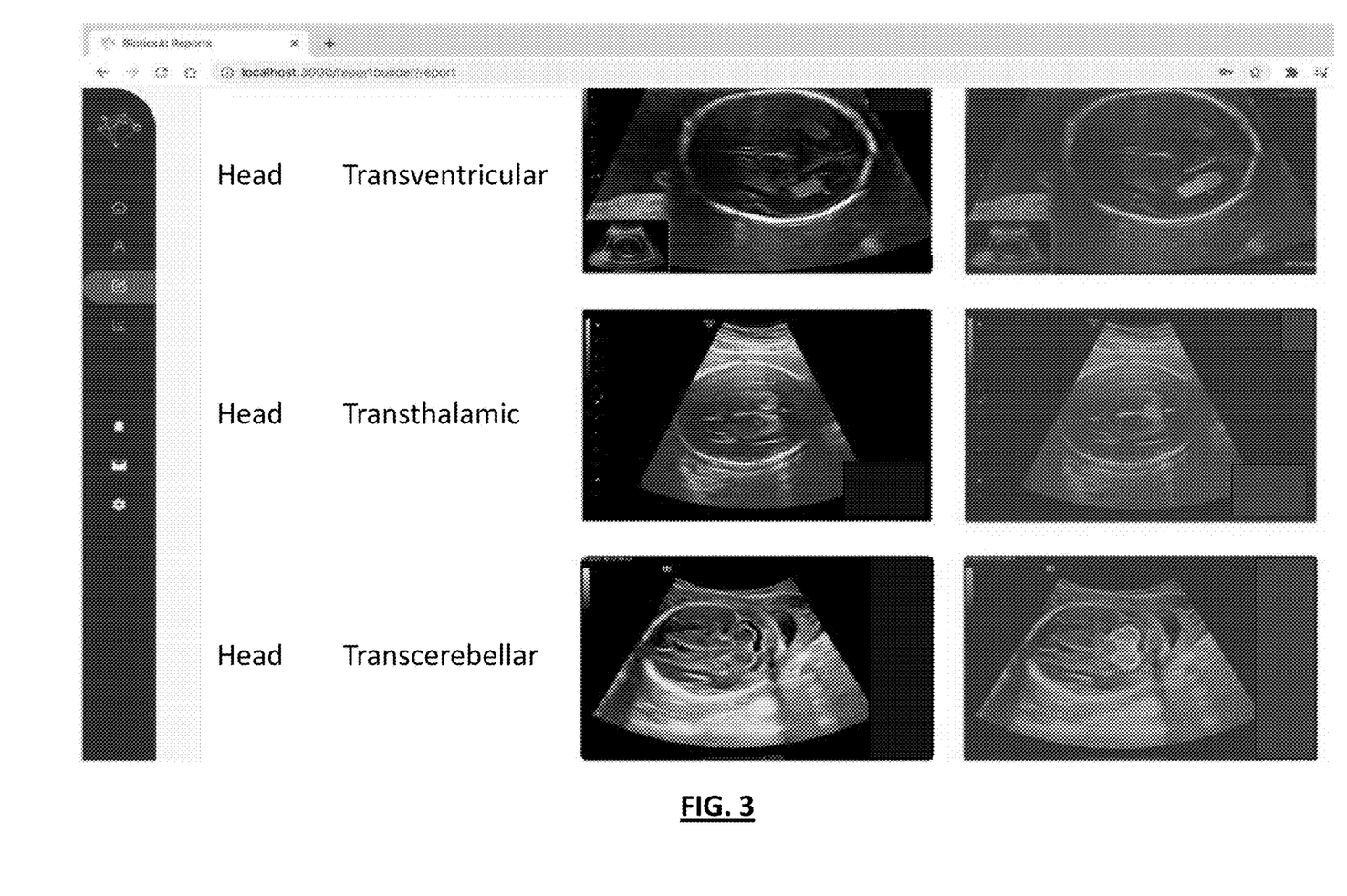
FIG. 3 is a view of a sample report output of a classification in accordance with certain embodiments.

Platform 120 further includes automatic report generator 228 for generating reports. In certain embodiment, reports preferably pertain to second trimester anatomical ultrasound scans and reflect the outcomes from the classifications by classifiers 224 and 226. FIG. 3 shows a report output of such classification in accordance with certain embodiments.

Other reports can be non-ML/AI based, for example using templates stored at template store 230. In such situations, the user can either manually enter data points or import data points from other sources, such as a medical practice's Electronic Health Record (EHR) system and/or Picture Archiving and Communication System (PACS).

Platform 120 allows users to easily share their generated reports with other medical professionals. In certain embodiments, created reports can be exported into the clinic EHR, HIS, and PACS systems, and/or they can include imported patient and other data, for example from external EHR, HIS, and PACS systems. The system can automatically push reports to relevant personnel, for example specialists whose additional expertise may be required.

Figure 4:
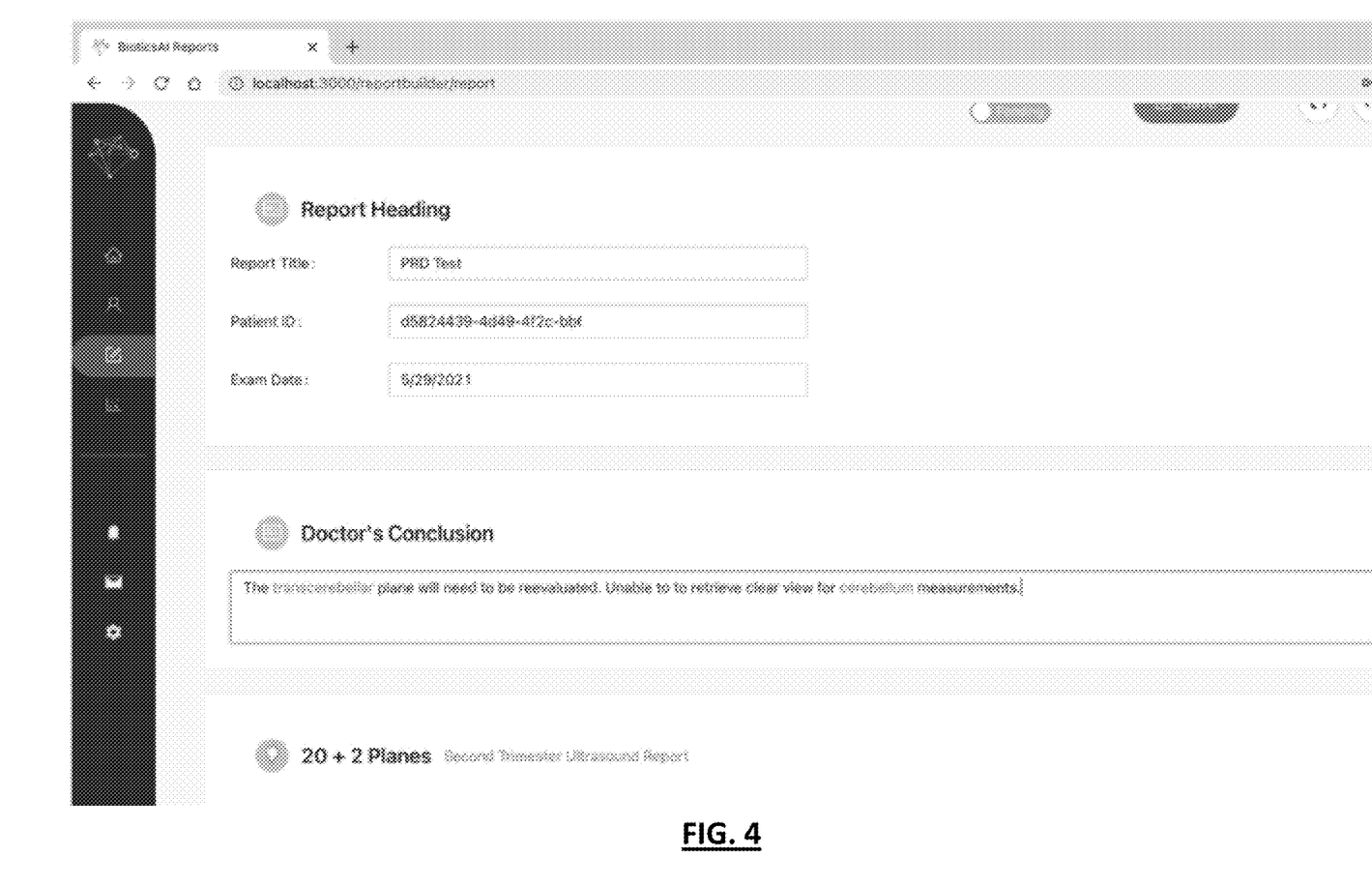
FIG. 4 is a snapshot of a commented report in accordance with certain embodiments.

By way of front-end subsystem 210, users are able to add customized comments on the reports and share a generated report with other medical professionals in their practice (for example sonographers, OB/GYNs, and others). Those medical professionals can then review, comment on, and approve the reports in platform 120. FIG. 4 shows a snapshot of a commented report in accordance with certain embodiments.

Platform 120 also provides the user with the ability to select frames to save into a report from a video of an ultrasound scan. For second trimester ultrasound scan videos, as mentioned above, ML/AI subsystem 220 can provide the user with timestamps in which specific cross-sectional planes (from the "20+2 planes" scan) are detected in the video.

Another feature of platform 120 is that it provides the user with the ability to generate patient-friendly reports. In certain embodiments, these reports provide additional context and describe medical terms in language easily understandable by a non-medical professional.

Some advantages of system 110 include:
1. Reduce time taken in a clinic to generate reports.
2. Ease manual report creation & sharing.
3. Facilitate communication between medical professionals,
4. Ease the process of finding and capturing planes in ultrasound videos.
5. Automate visual data point retrieval & archiving.
6. Improve patient experience and empower patients with prenatal knowledge.

Machine Learning/Artificial Intelligence Model

As mentioned above, ML/AI subsystem 220 comprises an ML/AI engine 222 having classifier modules 224 and 226 that are responsible for accepting input data points (for example video or a picture) and returning two outputs:
1. The anatomical plane associated with each image (or frame in a video), as determined by the 20+2 classifier 224, and
2. The key anatomical regions and their location in the image (specified by annotating the pixels in the image that represent a key anatomical region), as determined by the anatomical structure classifier 226.

In certain embodiments, the ML/AI process and framework for performing these tasks entails the following:

Data Preparation

Prior to training/testing, data is deduplicated and anonymized by removing references to patient names in the ultrasound images. In one example, the data is collected through a research facility which aggregated data from 3 separate sites. A team of 15 obstetric professionals annotated the images. In certain embodiments, images were annotated by 1 annotator and later validated by at least 2 additional annotators.

Model Overview
  AI (1)—Plane Classification Model: this machine learning model is responsible for identifying and classifying individual fetal cross-sectional planes from a second trimester, fetal ultrasound screening image. Example: Image is classified as the transcerebellar plane
  AI (2)—Semantic Segmentation Model: this model is responsible for detecting and highlighting specific anatomical regions in a fetal ultrasound screening image. Example: Cerebellum, Cisterna Magna, and Cerebral peduncles
  AI (3)—Abnormality Flagging Model: this machine learning model is responsible for identifying and classifying a fetal ultrasound plane image as either normal or abnormal.

Model Input and Output

Inputs
  For AI(1), AI(2) and AI(3), the model's input is a fetal ultrasound image or a frame from a fetal ultrasound screening video.
  For AI(3) the input is a fetal ultrasound image associated with one of the 20 standard cross sectional fetal ultrasound views captured as part of a second trimester anatomical screening. These images can be cross sectional views of any of the following anatomical planes:

List 1: 20 Planes
- Spine—saggital Complete w/Skin
- Spine—spine coronal complete
- Fetal Body Coronal Section
- Head—transventricular
- Head—transthalamic
- Head—transcerebellar
- Thorax—lungs four heart chambers
- Thorax—LVOT
- Thorax—RVOT
- Thorax—3vt view of heart
- Abdomen—Stomach Umbilical Vein
- Abdomen—Cord Insertion
- Abdomen—Kidneys
- Abdomen—bladder
- Limbs—femur
- Limbs—legs & feet
- Limbs—Arms & hands
- Face—coronal of upper lip, nose and nostrils
- Face—orbits/lenses
- Face—median facial profile Outputs For AI(1), the output of the model is the plane that the frame belongs to (or "non-plane" if it does not belong to a particular plane). The list of possible planes can be seen in the "List 1" above.

For AI(2), the output of the model is a segmentation mask wherein each pixel is classified with an anatomical region.

Figure 5:
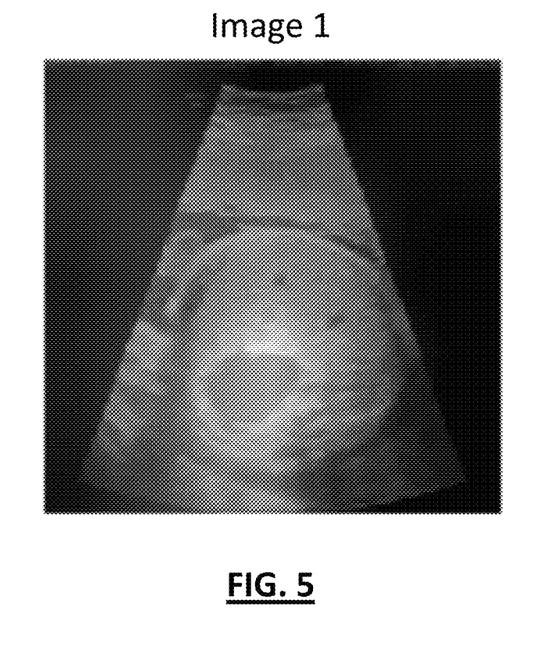
FIG. 5 is an example heatmap localizing an abnormality in accordance with certain embodiments.

For AI(3), the output of the model is a classification of the image as either normal or abnormal and a "heatmap" depicting where in the image was most relevant to determining if an abnormality exists. Image 1 shown in FIG. 5 is an example heatmap localizing an abnormality in accordance with certain embodiments.

Model Development

In certain embodiments, all models were developed in python using fastai and PyTorch frameworks.

AI(1)
- Use a Resnet model pre-trained on imagenet with a cyclic learning rate between 0.00002 and 0.002.
- For an optimizer, use Adam with momentum=0.9, sqr_mom=0.99, eps=0.00001 and wd=0.01.
- For hyperparameter tuning, aside from learning rate, use fastai's default hyperparameters.
- Brightness, contrast and saturation transforms are applied during training time as well as rotating and zooming.
- No post-processing was applied to the output of the model (e.g. nms).

AI(2)
- A Unet model with a pre-trained resnet backbone and a cyclic learning rate between 0.000001 and 0.0001 is used.
- For an optimizer, Adam with momentum=0.9, sqr_mom=0.99, eps=0.00001 and wd=0.01 is used.
- Learning rate was is determined using fastai's learning rate finder and for other hyperparameters, defaults are used.
- Brightness, contrast and saturation transforms are used during training time as well as rotating and zooming.
- No post-processing is applied to the output of the model (e.g. nms).

AI(3)
- A resnet model pre-trained on imagenet with a multilabel classification head is used.
- A cyclic learning rate between 0.00003 and 0.0003 is used, and an Adam optimizer with momentum=0.9, sqr_mom=0.99, eps=0.00001 and wd=0.01 (library defaults).
- Learning rate determined using fastai's learning rate finder; and for other hyperparameters, defaults are used.
- Brightness, contrast and saturation transforms are applied during training time as well as rotating and zooming.
- No post-processing is applied to the output of the model (e.g. nms).

Additional Notes about Model Development

No ensemble methods (weighted average results of multiple models) were used for AI(1), AI(2) or AI(3).

Figure 6:
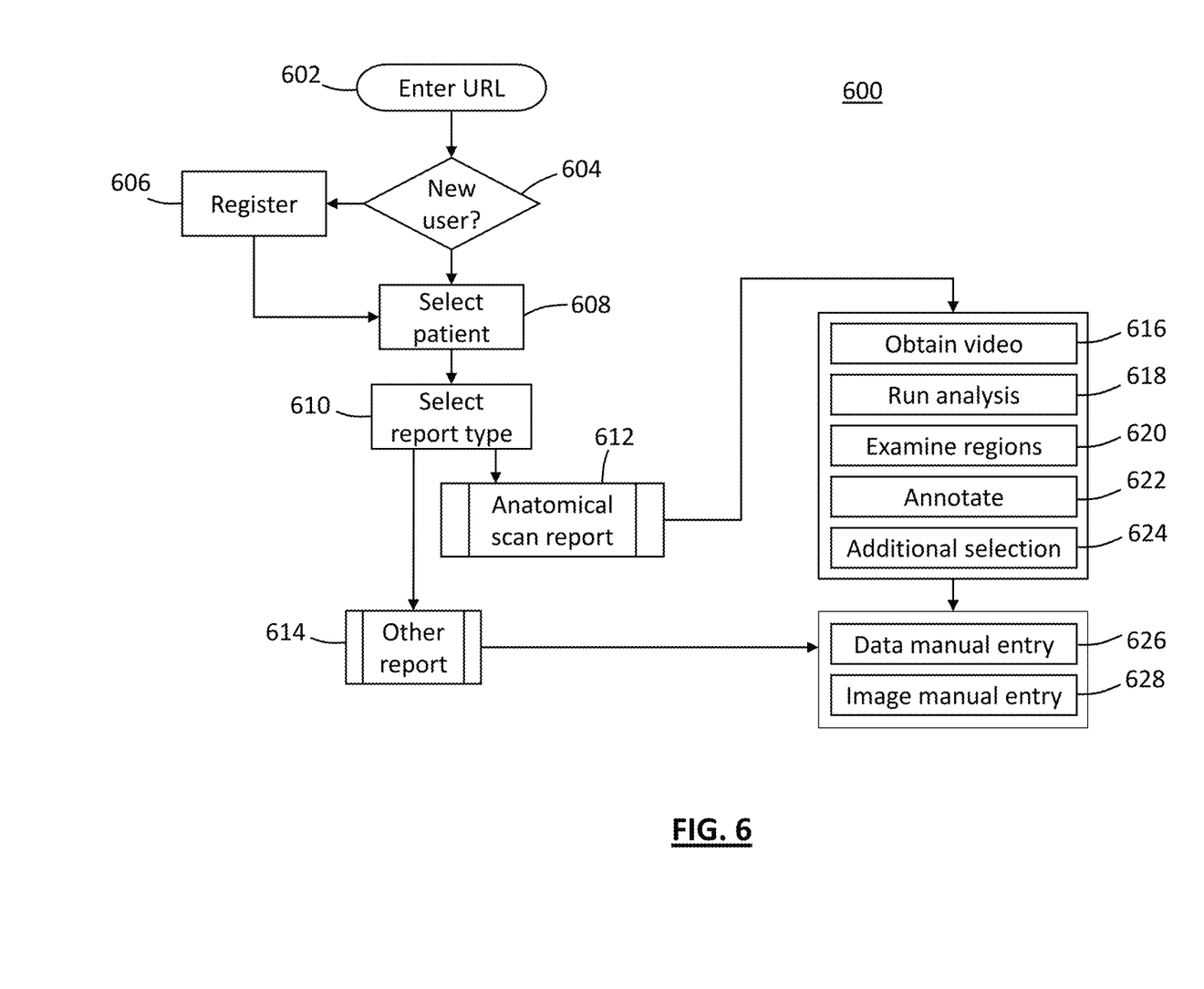
FIG. 6 is a flow diagram of a typical clinical work flow session experienced by a user of the platform 120.

FIG. 6 is a flow diagram of a typical clinical work flow session experienced by a user of the platform 120, who may be for example a medical professional such as an OB/GYN. All steps and interactions are HIPAA-compliant. At 602, the user navigates a browser to the associated URL to gain access to the platform. At 604, it is determined if the user has proper credentials or is a new user, and is prompted to register at 606 if new, and is then logged in. Once the user is logged in, the user selects, at 608, the patient of interest. The patient selection is facilitated by the platform's interaction with the EHR system available at the practice. The platform 120 can make requests to the EHR system (or systems) to retrieve patient information. In certain embodiments, the platform 120 does not store any patient PII as a result of this retrieval.

At 610, the user selects the desired report type. For example, the user can select a second trimester anatomical scan report, at 612, which allows the user to do one or more of the following:
- Upload an image or video of a scan from their computer to the web service comprising platform 120, and/or select a video of the scan from a list retrieved from a PACS or similar system, at 616.
- Run an analysis of this video and examine the different cross-sectional planes of the fetus detected, at 618.
- Examine, within each cross-sectional plane, the anatomical regions of the fetus detected in that plane, at 620.
- Add a text conclusion note to the report, at 622.
- For a given cross-sectional plane, select a different frame from the ultrasound scan video, at 624.

Alternatively or in addition, the user can select a different kind of report, at 614. For example, a custom-built report, using standardized templates, can be configured by the user. Such a report can use manually-entered data (at 626) and manually-selected images (at 628) from a PACS system. In certain embodiments, the user also has the option of manually entering data and manually selecting images even when a second trimester anatomical scan report is chosen a 612.

In accordance with certain embodiments, system 100 enables medical personnel, for example OB/GYNs, to view a list of pending report approvals and/or a list of patient referrals sent to the OB/GYN. It allows capture of selected frames of interest from a fetal ultrasound video, for example for replacement with an AI selected image, or to add an image to the report.

ML/AI subsystem 220 can be used to classify each frame of a fetal ultrasound video presented to the OB/GYN, by plane from the 20+2 planes classifier 224, to save time selecting the appropriate image to be included in a report.

The platform 120 allows easy navigation to any part of the application via search, and allows review and approval of reports where the peer review has been assigned to the medical professional.

The system also allows defining automated peer review relationships between medical care professionals, defining automated patient referrals for maternal fetal medicine doctors for example, and referral of high risk patients to maternal fetal medicine doctors.

In addition, medical care professionals using system 100 can query an EHR system for patients and add them to a patient board; begin generating a report for a patient from the patient's board; and access a patient's profile for viewing and updating all associated reports. Patients can also be queried via the PACS systems.

Medical care professionals are also able to select a reporting template, for example for filling out a patient chart post prenatal test. ML/AI can be applied to automatically process ultrasound videos and images by selecting each of the 20 planes and organizing them in a table. ML/AI can also be applied to automatically detect & document the individual anatomical regions of a fetus that were reviewed in an ultrasound screening. ML/AI models can be used to review each ultrasound image for image anomalies (image problems which could be a result of image quality issues or fetal abnormalities—source will not specified), and flag any images which classify as having a "potential image quality issue" in the final report. Reports can be submitted under a "pending approval" state, so that they can be validated by an OB/GYN doctor.

The system 100 can also be used to provide a list of patient reports for viewing in detail, or for filtering through reports by trimester to easily find a target report.

In addition to viewing and commenting on current patient reports, system 100 permits viewing a history of updates made on a patient's report; exporting reports to PDF for use in existing report sharing workflows; electronically sharing a report with other medical care professionals; and generating a "patient friendly report", which provides a patient with full details of the anatomical scan in layman's terms to describe complex medical information.

While embodiments and applications have been shown and described, it would be apparent to those skilled in the art having the benefit of this disclosure that many more modifications than mentioned above are possible without departing from the inventive concepts disclosed herein. The invention, therefore, is not to be restricted based on the foregoing description. This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative.

What is claimed is:

1. A system for aggregating, analyzing, and reporting medical information comprising:
    a front end module, operating on a computing device, for managing a user interface;
    a back end module, operating on the computing device, for exchanging patient information with a clinic record system and obtaining one or more medical images therefrom;
    a machine learning/artificial intelligence (ML/AI) engine, operating on the computing device, for analyzing said one or more medical images and generating analysis results, wherein the ML/AI engine further comprises:
        a plane classification model that identifies and classifies fetal-cross sectional planes from the one or more medical images;
        an anatomical structural classifier that applies semantic segmentation to associate specific pixels of the one or more images with corresponding anatomical structures of a given fetal-cross-sectional plane by classifying each pixel; and
        an abnormality flagging model that classifies the one or more images as abnormal and identifies a subset of the specific pixels associated with an anatomical structure as abnormal;
    a report generator, operating on the computing device, for generating a report that includes said analysis results.

2. The system of claim 1, wherein the machine learning/artificial intelligence (ML/AI) engine applies rules that are encoded as weight matrices configured to operate on fetal ultrasound images.

3. The system of claim 2, wherein the weigh matrices are generated by:
    a) pre-training on a large general public image dataset,
    b) additional pre-training on a general fetal ultrasound image dataset using self-supervised learning,
    c) re-architecting final layers of a pre-trained convolutional neural network from a) and b), and
    d) creating multiple output heads to classify fetal planes, fetal abnormalities, fetal anatomical structures, and diagnostic utility, and
    e) fine-tuning using an annotated dataset of second trimester fetal ultrasound images.

4. The system of claim 1, wherein the plane classifier is an anatomical plane classifier and the given fetal-cross sectional plane is an anatomical plane.

5. The system of claim 4, wherein the anatomical plane classifier is a 20+2 classifier.

6. The system of claim 1, wherein the back end module includes API functionality activated from front end module.

7. The system of claim 1, wherein the clinic record system is one or both of a PACS and EMR system.

8. The system of claim 1, wherein the exchange of patient information is by way of a DICOMWeb API.

9. The system of claim 1, wherein the patient information includes DICOM studies and/or DICOM structured reports.

10. The system of claim 1, wherein the ML/AI provides a timestamp output of analyzed images.

11. The system of claim 1, wherein the ML/AI engine is operable to flag images with quality issues.

12. The system of claim 1, wherein the report pertains to second trimester anatomical ultrasound scans.

13. The system of claim 1, wherein the report includes template-based information.

14. A method for generating an anatomical scan report comprising:
    selecting a patient;
    obtaining a fetal scan associated with the patient;
    conducting an analysis of the fetal scan using a machine learning/artificial intelligence (ML/AI) engine operating on a computing device and having multiple output heads further comprising:

an anatomical plane classification model that identifies and classifies a fetal-cross-section plane from the fetal scan, wherein the anatomical plane classification model is a resnet model;

an anatomical structure classifier that associates specific pixels of the fetal scan with corresponding anatomical structures within the fetal scan by classifying each pixel, wherein the anatomical structure classifier is a Unet model; and an abnormality flagging model that classifies the fetal scan as abnormal and identifies a subset of the specific pixels as abnormal in response to receiving the fetal scan and fetal-cross sectional plane, wherein the abnormality flagging model is another resnet model; and generating a report that includes results of said analysis including at least classification of of the image as abnormal.

15. The method of claim 14, wherein conducting an analysis of the fetal scan using the machine learning/artificial intelligence (ML/AI) engine comprises applying rules that are encoded as weight matrices configured to operate on fetal ultrasound images.

16. The method of claim 15, wherein the weight matrices are generated by:
 a) pre-training on a large general public image dataset,
 b) additional pre-training on a general fetal ultrasound image dataset using self-supervised learning,
 c) re-architecting final layers of a pre-trained convolutional neural network from a) and b), and
 d) creating the multiple output heads to classify fetal planes, fetal abnormalities, fetal anatomical structures, and diagnostic utility, and
 e) fine-tuning using an annotated dataset of second trimester fetal ultrasound images.

17. The method of claim 14, wherein said obtaining is from a clinic record system selected from one or both of a PACS and EMR system.

18. The method of claim 14, wherein the ML/AI engine provides a timestamp output of analyzed images.

19. The method of claim 14, wherein the ML/AI engine is operable to flag images with quality issues.

20. A method for generating an anatomical scan report comprising:
 selecting a patient;
 obtaining a fetal scan associated with the patient;
 conducting an analysis of the fetal scan using a machine learning/artificial intelligence (ML/AI) engine operating on a computing device and having multiple output heads further comprising:
 an anatomical plane classification model that identifies and classifies a fetal-cross-section plane from the fetal scan, wherein the anatomical plane classification model is a resnet model having a first output head;
 an anatomical structure classifier that associates specific pixels of the fetal scan with corresponding anatomical structures within the fetal scan by classifying each pixel of the fetal scan, wherein the anatomical structure classifier is a Unet model having a second output head; and
 an abnormality flagging model that outputs a classification of the fetal scan as abnormal and a heatmap of the fetal scan marking pixels of the fetal scan as relevant to the abnormality classification in response receiving the fetal scan and fetal-cross sectional plane, wherein the abnormality flagging model is another resnet model having a third output head; and
 generating a report that includes results of said analysis including at least classification of of the image as abnormal.

* * * * *